US010076245B2

(12) United States Patent
Baba et al.

(10) Patent No.: US 10,076,245 B2
(45) Date of Patent: Sep. 18, 2018

(54) SPECIMEN INFORMATION ACQUISITION APPARATUS AND SPECIMEN INFORMATION ACQUISITION METHOD

(75) Inventors: Yoshitaka Baba, Tokyo (JP); Jiro Tateyama, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 434 days.

(21) Appl. No.: 14/126,814

(22) PCT Filed: Jun. 12, 2012

(86) PCT No.: PCT/JP2012/003826
§ 371 (c)(1),
(2), (4) Date: Dec. 16, 2013

(87) PCT Pub. No.: WO2012/176400
PCT Pub. Date: Dec. 27, 2012

(65) Prior Publication Data
US 2014/0121518 A1    May 1, 2014

(30) Foreign Application Priority Data

Jun. 22, 2011 (JP) ................................ 2011-138797

(51) Int. Cl.
*A61B 8/00* (2006.01)
*A61B 5/00* (2006.01)
(Continued)

(52) U.S. Cl.
CPC .......... *A61B 5/0035* (2013.01); *A61B 5/0095* (2013.01); *A61B 8/145* (2013.01);
(Continued)

(58) Field of Classification Search
CPC ... A61B 5/0035; A61B 8/4483; A61B 8/5207; A61B 8/463; A61B 8/4416; A61B 8/145; A61B 5/0095; A61B 2562/046
See application file for complete search history.

(56) References Cited

U.S. PATENT DOCUMENTS

2005/0004458 A1*  1/2005  Kanayama ........... A61B 5/0091
                                                         600/437
2005/0187471 A1    8/2005  Kanayama et al.
(Continued)

FOREIGN PATENT DOCUMENTS

EP        1561424 A1    8/2005
JP     2005-021380 A    1/2005
(Continued)

*Primary Examiner* — Jonathan Cwern
(74) *Attorney, Agent, or Firm* — Canon U.S.A., Inc. IP Division

(57) ABSTRACT

A specimen information acquisition apparatus includes a signal processor which can selectively operate in first and second modes. In the first mode, when a first group represents a group of devices among receiving devices and a second group represents at least a fraction of a group of devices other than the first group, a photoacoustic image and an ultrasonic image are obtained based on received signals from the first group and the second group, respectively. In the second mode, when a third group represents a group of devices having at least a fraction of a group of devices other than the first group and a fourth group represents at least a fraction of a group of devices other than the third group, a photoacoustic image and an ultrasonic image are obtained based on received signals from the third group and the fourth group, respectively.

26 Claims, 18 Drawing Sheets

(51) Int. Cl.
*A61B 8/14* (2006.01)
*A61B 8/08* (2006.01)

(52) U.S. Cl.
CPC .......... *A61B 8/4416* (2013.01); *A61B 8/4483* (2013.01); *A61B 8/463* (2013.01); *A61B 8/5207* (2013.01); *A61B 2562/046* (2013.01)

(56) References Cited

U.S. PATENT DOCUMENTS

| | | | |
|---|---|---|---|
| 2008/0221647 A1* | 9/2008 | Chamberland | A61B 5/0095 607/88 |
| 2009/0187099 A1 | 7/2009 | Burcher | |
| 2010/0268058 A1* | 10/2010 | Chen | A61B 5/0086 600/407 |
| 2011/0088477 A1 | 4/2011 | Someda et al. | |
| 2011/0106478 A1 | 5/2011 | Someda | |
| 2011/0128816 A1 | 6/2011 | Baba et al. | |
| 2011/0208057 A1* | 8/2011 | Oikawa | A61B 5/0095 600/443 |

FOREIGN PATENT DOCUMENTS

| | | |
|---|---|---|
| JP | 2010022816 A | 2/2010 |
| WO | 2009154244 A1 | 12/2009 |
| WO | 2009154298 A1 | 12/2009 |
| WO | 2010074104 A1 | 7/2010 |

\* cited by examiner

FIG. 7
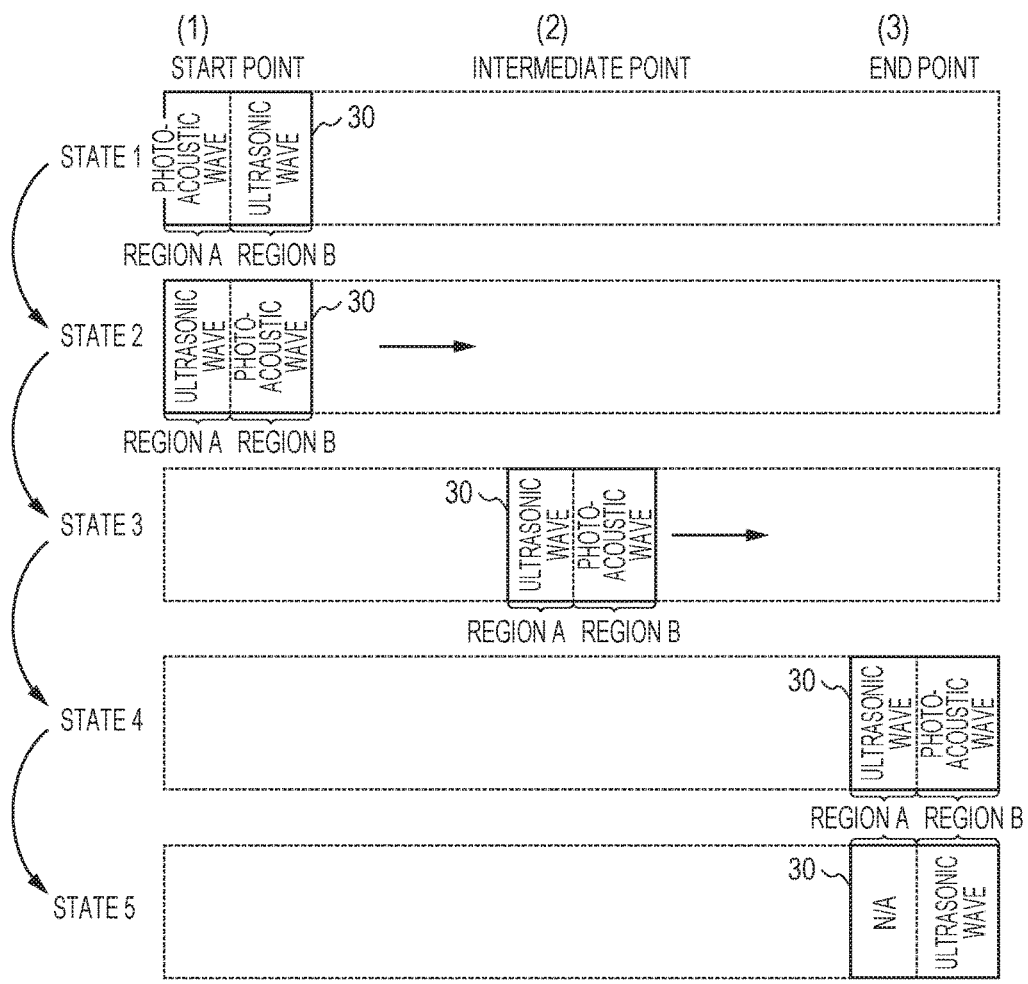

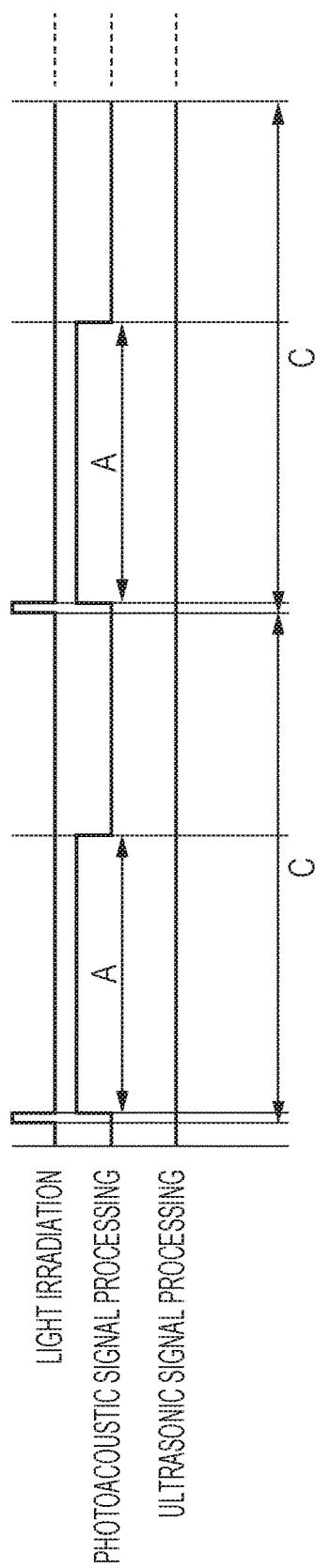

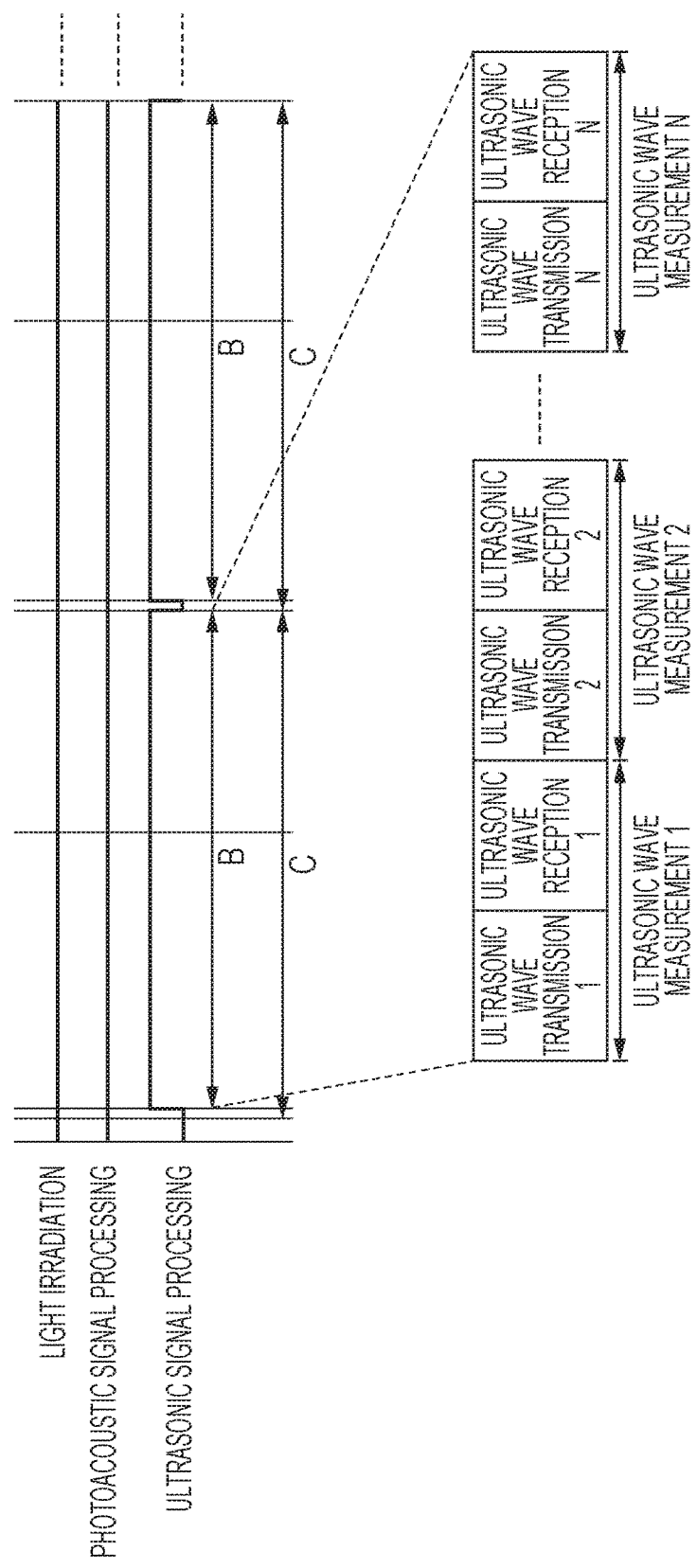

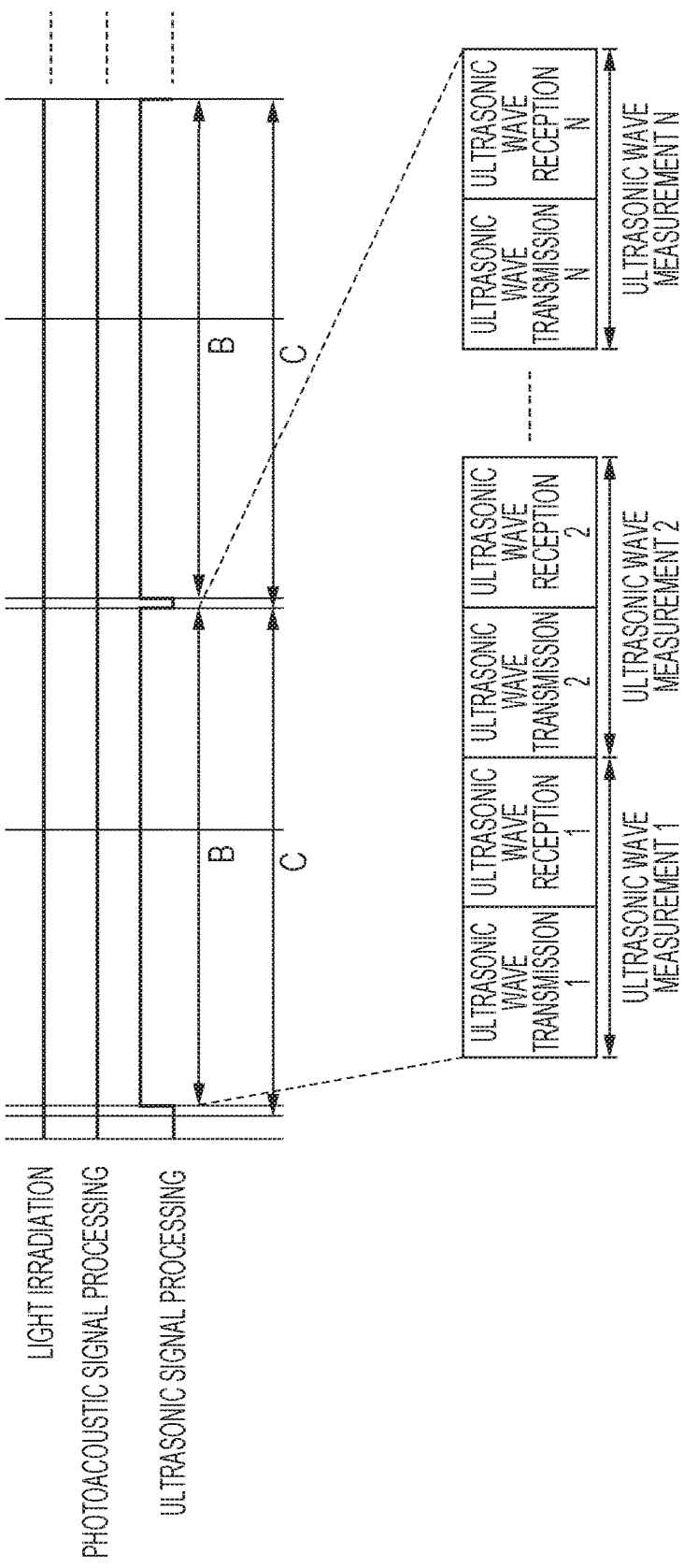

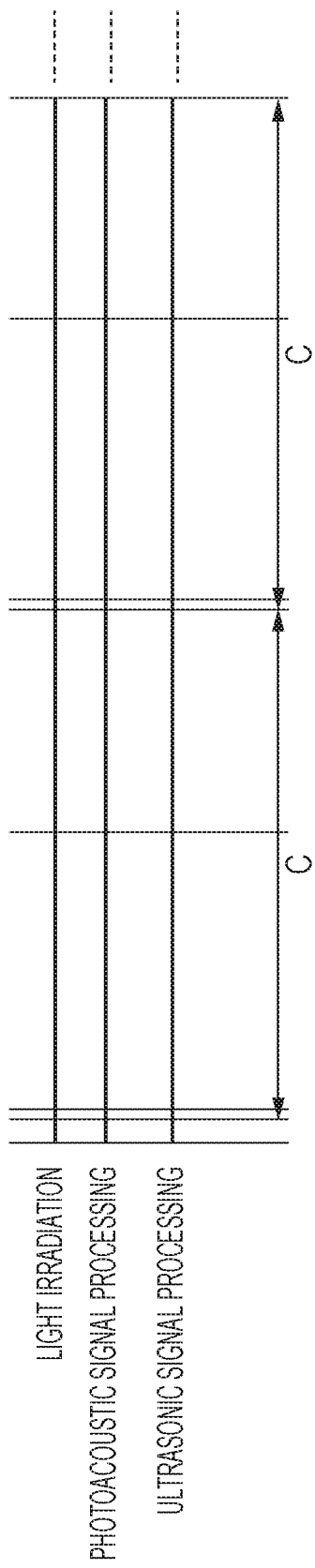

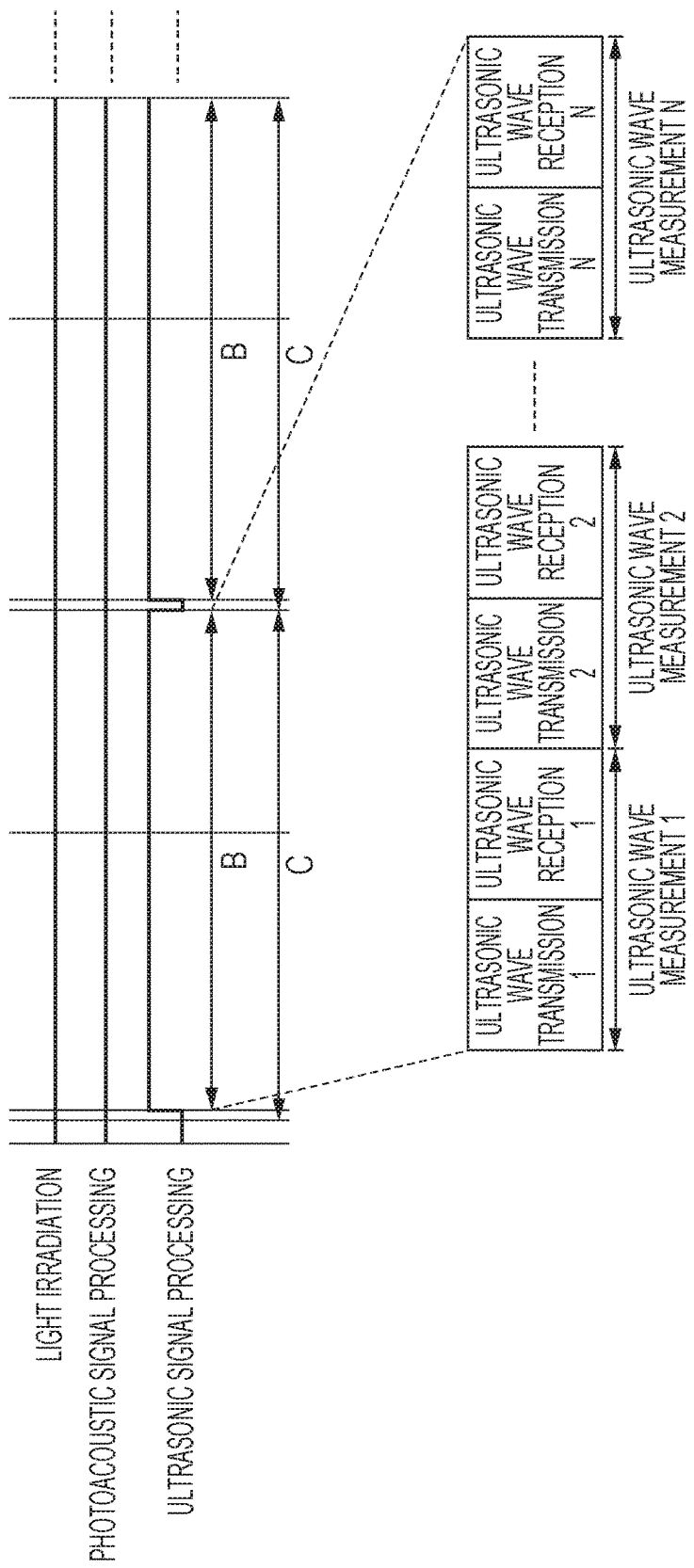

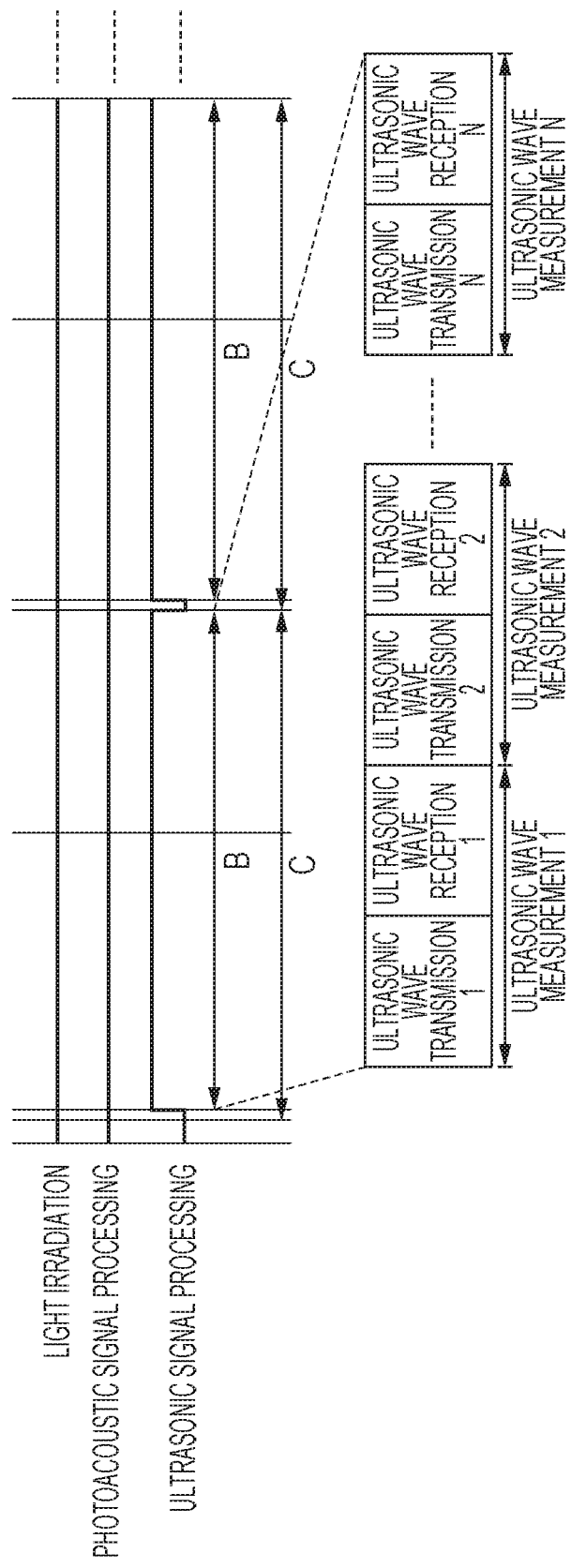

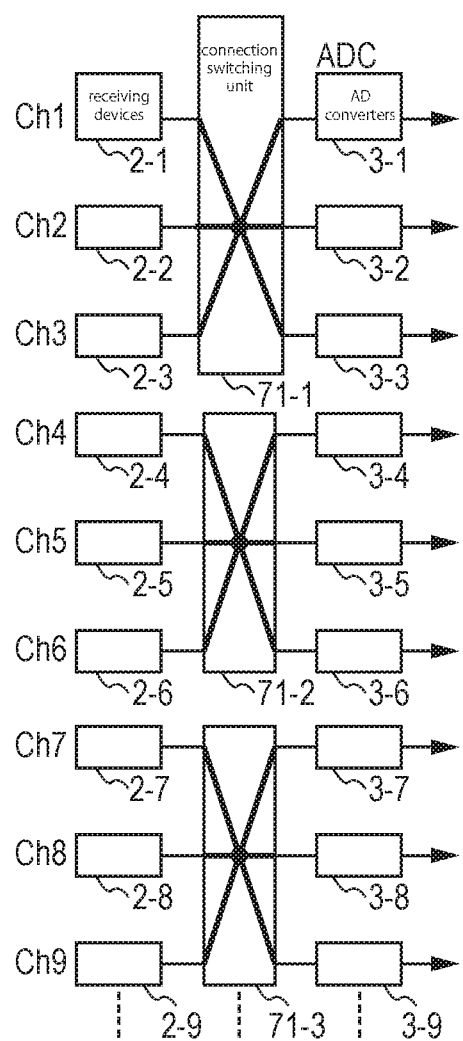

SPECIMEN INFORMATION ACQUISITION APPARATUS AND SPECIMEN INFORMATION ACQUISITION METHOD

CROSS-REFERENCE TO RELATED APPLICATIONS

This application is the U.S. National Stage of, and claims the benefit of, International Application No. PCT/JP2012/003826, having international filing date Jun. 12, 2012, which claims priority from Japanese Patent Application No. 2014-156795, filed Jul. 31, 2014, and No. 2015-120404, filed Jun. 15, 2015.

TECHNICAL FIELD

The present invention relates to a specimen information acquisition apparatus and a specimen information acquisition method for forming a photoacoustic image or an ultrasonic image by irradiating a specimen with light or ultrasonic waves and receiving ultrasonic waves from the specimen.

BACKGROUND ART

Heretofore, it has been known that, when a living body is irradiated with light, photoacoustic waves (typically, ultrasonic waves) are produced due to an increase in temperature and thermal expansion of the tissues of the living body which are caused by optical absorption of the living body. Attempts have been made to apply photoacoustic imaging, in which the inside of a living body is visualized in a non-invasive manner by using photoacoustic signals which are received signals of the photoacoustic waves, to clinical practice. The definition of the lower limit of the frequency band of an ultrasonic wave is not always definite. However, an elastic wave of 20 kHz or more is herein called "an ultrasonic wave".

In addition, it has been expected that diagnostic accuracy in clinical practice can be markedly increased by combining photoacoustic imaging with ultrasonic imaging in which an ultrasonic image is generated by using ultrasonic signals which are received signals of the reflected waves of ultrasonic waves transmitted to a specimen.

As a probe with which photoacoustic imaging and ultrasonic imaging can be combined as described above, a probe has been proposed in which a transducer array for receiving photoacoustic waves and a transducer array for transmitting/receiving ultrasonic waves are arranged in parallel (see PTL 1).

CITATION LIST

Patent Literature

PTL 1: Japanese Patent Laid-Open No. 2010-22816

SUMMARY OF INVENTION

Technical Problem

However, a difference occurs between a reception region for reception of photoacoustic waves and a reception region for transmission/reception of ultrasonic waves in the probe described in PTL 1. This results in a decrease i the image quality of a photoacoustic image and an ultrasonic image.

Accordingly, the present invention provides a specimen information acquisition apparatus having a novel configuration and a specimen information acquisition method which can reduce a difference between a reception region for photoacoustic waves and a reception region for ultrasonic waves.

Solution to Problem

To solve the above-described problem, a specimen information acquisition apparatus of the present invention includes a signal processor which can selectively operate in a first mode and a second mode. In the first mode, when a group of devices among receiving devices is represented by a first group and at least a fraction of a group of devices among the receiving devices other than the first group is represented by a second group, a photoacoustic image is obtained on the basis of received signals that are output from the first group, and an ultrasonic image is obtained on the basis of received signals that are output from the second group. In the second mode, when a group of devices having at least a fraction of a group of devices among the receiving devices other than the first group is represented by a third group and at least a fraction of a group of devices among the receiving devices other than the third group is represented by a fourth group, a photoacoustic image is obtained on the basis of received signals that are output from the third group, and an ultrasonic image is obtained on the basis of received signals that are output from the fourth group.

Advantageous Effects of Invention

The present invention can provide a specimen information acquisition apparatus which has a novel configuration and which can reduce a difference between a reception region for photoacoustic waves and a reception region for ultrasonic waves.

BRIEF DESCRIPTION OF DRAWINGS

FIG. 7 is a diagram illustrating receiving situations which occur in the specimen information acquisition apparatus according to the first embodiment of the present invention.

FIG. 8A is a diagram illustrating an operating sequence of the specimen information acquisition apparatus in State 1 illustrated in FIG. 7.

FIG. 8B is a diagram illustrating an operating sequence of the specimen information acquisition apparatus in State 1 illustrated in FIG. 7.

FIG. 9A is a diagram illustrating an operating sequence of the specimen information acquisition apparatus in States 2 to 4 illustrated in FIG. 7.

FIG. 10A is a diagram illustrating an operating sequence of the specimen information acquisition apparatus in State 5 illustrated in FIG. 7.

FIG. 10B is a diagram illustrating an operating sequence of the specimen information acquisition apparatus in State 5 illustrated in FIG. 7.

FIG. 11A is a diagram illustrating another exemplary operating sequence of the specimen information acquisition apparatus in States 2 to 4 illustrated in FIG. 7.

FIG. 13B is a diagram illustrating connection switching units and their connection states according to the second embodiment of the present invention.

DESCRIPTION OF EMBODIMENTS

In ultrasonic imaging, an ultrasonic wave is typically transmitted to a region of a specimen which corresponds to one line that is constituted by two-dimensional pixels or three-dimensional voxels which are arranged in the specimen depth direction in one dimension, whereby the reflected wave of the ultrasonic wave which contains information about the one-line region is received. An ultrasonic image corresponding to the one-line region is generated on the basis of the received signal. At that time, an ultrasonic image is generated for the one-line region that is located in front of a reception region which has received the reflected wave of the ultrasonic wave. Therefore, it is difficult to obtain an ultrasonic image of a region other than the region that is located in front of the reception region.

In photoacoustic imaging, photoacoustic waves which are produced from a region corresponding to multiple lines are received, and the region corresponding to the lines is imaged on the basis of the received signals so that a photoacoustic image is generated. However, since a receiving device which receives a photoacoustic wave has directivity, the received signal of a photoacoustic wave that enters the detection surface of the receiving device at a certain angle is weakened. Accordingly, a photoacoustic image of a region other than the region that is located in front of the reception region which receives photoacoustic waves has low quantitativity.

As described above, when a difference occurs between a reception region used to obtain a photoacoustic image and a reception region used to obtain an ultrasonic image, degradation or a missing portion of the photoacoustic image and the ultrasonic image occurs.

Accordingly, it is desirable to reduce a difference between a reception region which receives photoacoustic waves and a reception region which receives the reflected waves of ultrasonic waves.

To achieve this, the inventors have devised a specimen information acquisition apparatus in which switching between the following modes can be performed at any timing for a received signal that is output from a receiving device: a mode in which signal processing is performed to obtain a photoacoustic image and a mode in which signal processing is performed to obtain an ultrasonic image.

Specimen information acquisition apparatuses according to embodiments of the present invention will be described in detail below with reference to the drawings.

First Embodiment

Figure 1:
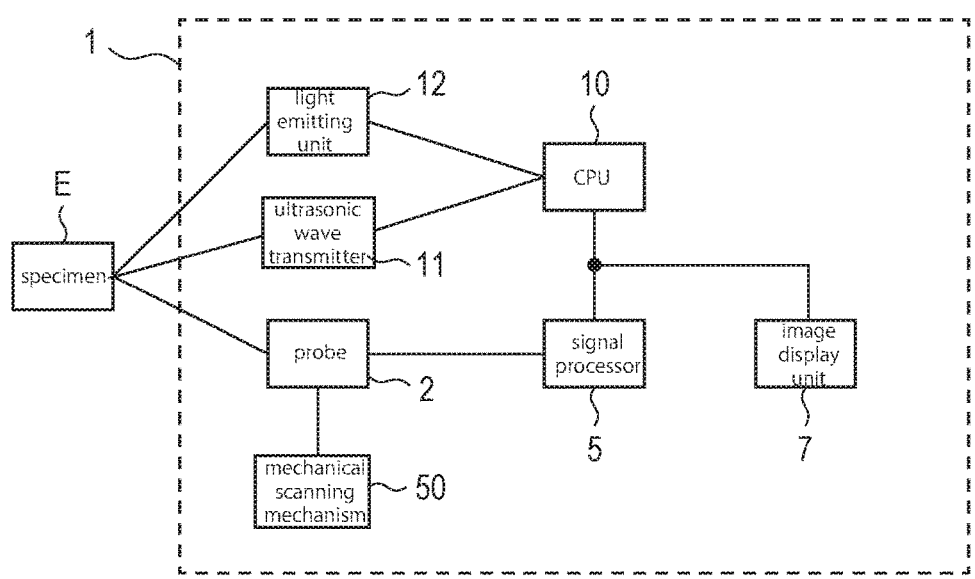
FIG. 1 is a diagram illustrating a configuration of a specimen information acquisition apparatus according to a first embodiment of the present invention.

FIG. 1 is a diagram illustrating a configuration of a specimen information acquisition apparatus 1 according to a first embodiment of the present invention.

The specimen information acquisition apparatus 1 illustrated in FIG. 1 includes a probe 2 including multiple receiving devices, a signal processor 5, an image display unit 7, a central processing unit (CPU) for control 10, an ultrasonic wave transmitter 11 including multiple transmitting devices, a light emitting unit 12, and a mechanical scanning mechanism 50 serving as a moving unit. The signal processor 5 may be included in the probe 2.

The light emitting unit 12 irradiates a specimen E with light at certain timing under control performed by, for example, the CPU for control 10. When the specimen E is irradiated with light by the light emitting unit 12, photoacoustic waves are produced in the specimen E.

The ultrasonic wave transmitter 11 transmits ultrasonic waves to the specimen E under the control performed by, for example, the CPU for control 10.

The receiving devices included in the probe 2 receive the photoacoustic waves produced in the specimen E and the reflected waves of the ultrasonic waves transmitted to the specimen E, and convert them into analog electric signals. According to the first embodiment, the ultrasonic wave transmitter 11 and the probe 2 are provided separately. Alternatively, the probe 2 may transmit ultrasonic waves.

Then, the signal processor 5 converts the analog electric signals which are output from the receiving devices into digital electric signals. The signal processor 5 then performs, for example, delay-and-sum processing, filtering processing, logarithmic compression, and envelope detection on the digital electric signals.

After that, the signal processor 5 performs necessary processing for image generation on the signals obtained through the above-described processing performed on the received signals, so as to generate image data, i.e., a photoacoustic image and an ultrasonic image.

The signal processor 5 performs adequate processing in accordance with whether the received signals are those of photoacoustic waves or the reflected waves of ultrasonic waves.

The sequence of the signal processing performed by the signal processor 5 is not limited to the sequence described in the first embodiment. For example, the digital conversion may be performed after the delay-and-sum processing.

Then, a photoacoustic image and an ultrasonic image are displayed on the image display unit 7 on the basis of the image data generated by the signal processor 5.

The CPU for control 10 supplies data and control signals which are necessary for control of the blocks.

Figure 2:
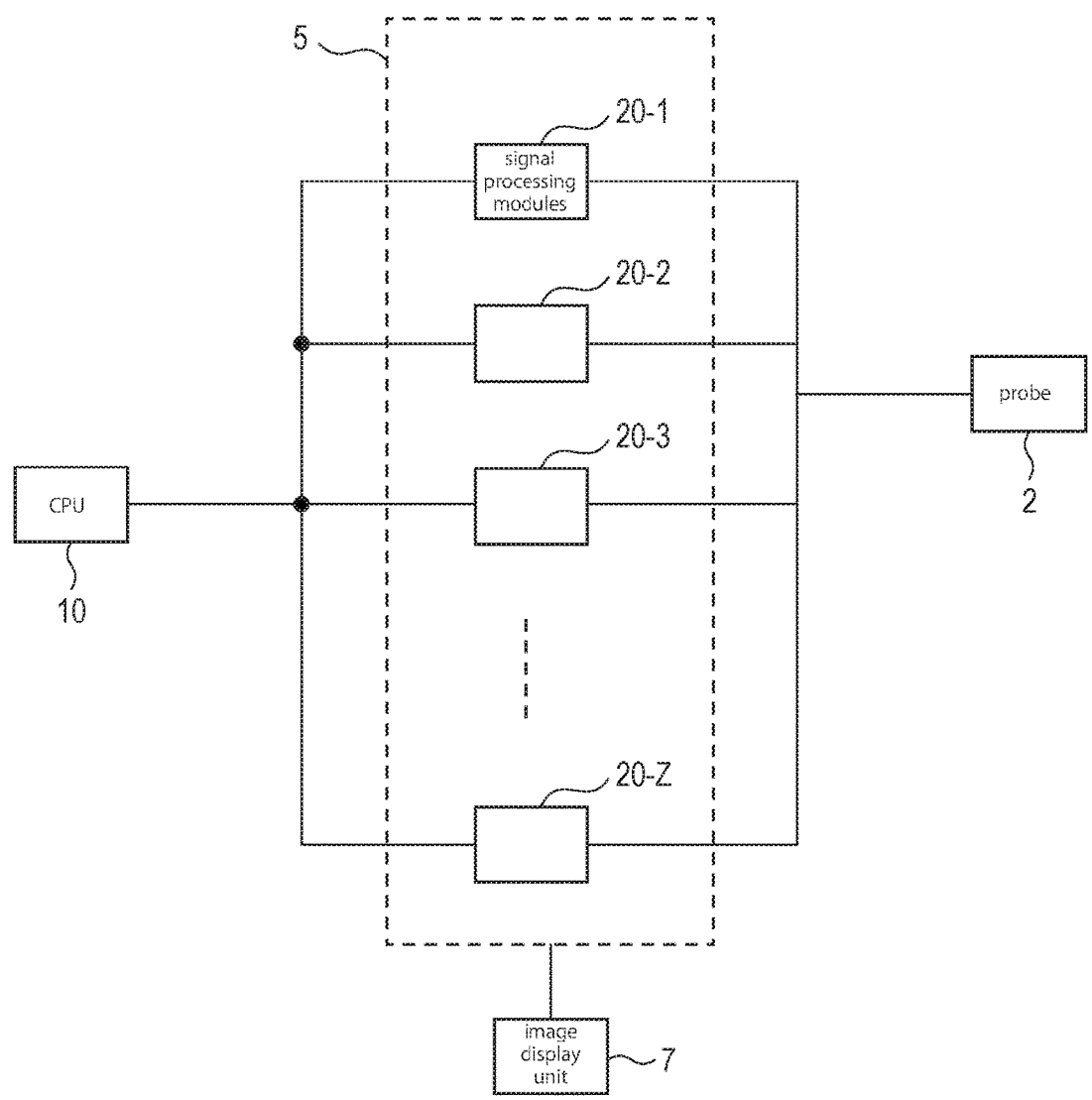
FIG. 2 is a diagram illustrating a configuration of a signal processor according to the first embodiment of the present invention.

FIG. 2 is a diagram illustrating the signal processor 5 according to the first embodiment of the present invention. The signal processor 5 includes signal processing modules 20-1 to 20-Z. Hereinafter, when either one of the signal processing modules 20-1 to 20-Z is designated without specifying one of the signal processing modules, the expression "signal processing module 20" is used.

Figure 3:
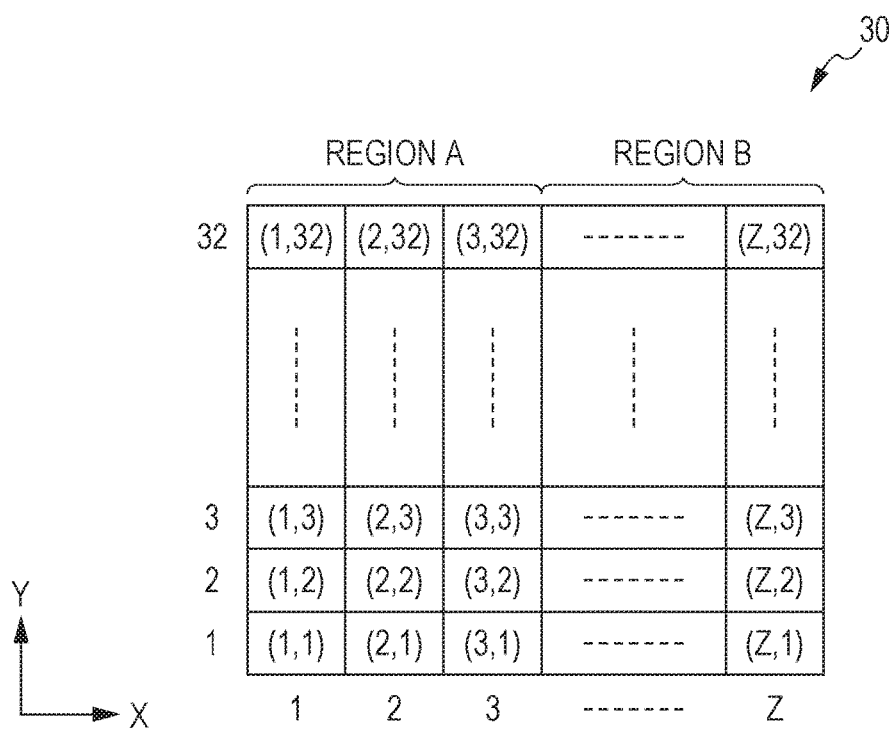
FIG. 3 is a diagram illustrating a configuration of a device array according to the first embodiment of the present invention.

FIG. 3 is a diagram illustrating a device array 30 included in the probe 2 according to the first embodiment. As illustrated in FIG. 3, the device array 30 includes multiple receiving devices (1, 1) to (Z, 32). As a receiving device, a piezoelectric element, a capacitive micromachined ultrasonic transducer produced through an application of the semiconductor processes, a Fabry-Perot resonator, and the like may be used. When the device array 30 which is to receive both of photoacoustic waves and the reflected waves of ultrasonic waves is taken into consideration, it is desirable to use a device having a broad frequency reception bandwidth as the device array.

Hereinafter, when either one of the receiving devices (1, 1) to (Z, 32) is designated without specifying one of the receiving devices, the expression "receiving device" is used. The device array 30 is desirably formed of a two-dimensional array.

The receiving devices (1, 1) to (Z, 32) illustrated in FIG. 3 are separated into groups, and the receiving devices in each group are connected to a corresponding one of the signal processing modules. For example, the receiving devices (1, 1) to (1, 32) are connected to the signal processing module 20-1; the receiving devices (2, 1) to (2, 32) are connected to the signal processing module 20-2; and the receiving devices (Z, 1) to (Z, 32) are connected to the signal processing module 20-Z.

The connection states in which the receiving devices are connected to the signal processing modules are not limited to this. For example, each of the receiving devices in the device array 30 may be connected to a corresponding one of the signal processing modules 20; or all of the receiving devices in the device array 30 may be connected to a single signal processing module 20. An optimal connection state may be selected as necessary.

A first feature of the present invention is to use multiple receiving devices which are separated into groups.

A second feature of the present invention is to switch signal processing performed on a signal received when any receiving device in the device array receives an acoustic wave. For example, according to the first embodiment, the CPU for control 10 illustrated in FIG. 2 controls signal processing modules 20 to perform switching of the signal processing, i.e., switching of a mode, on signals received in a certain reception region in the device array.

In a first mode according to the first embodiment, signal processing corresponding to photoacoustic waves is performed on signals received in a region A in FIG. 3; and signal processing corresponding to the reflected waves of ultrasonic waves which are transmitted from the specimen E is performed on signals received in a region B.

In a second mode, the signal processing corresponding to the reflected waves is performed on signals received in the region A; and the signal processing corresponding to photoacoustic waves is performed on signals received in the region B. These modes are controlled by the CPU for control 10 so that operations can be selectively made.

In the above-described example, the mode is switched for a region corresponding to each of the signal processing modules. Alternatively, as described below, an operation performed by each of the signal processing modules may be switched, enabling the mode for a region corresponding to a smaller unit to be switched.

Figure 4:
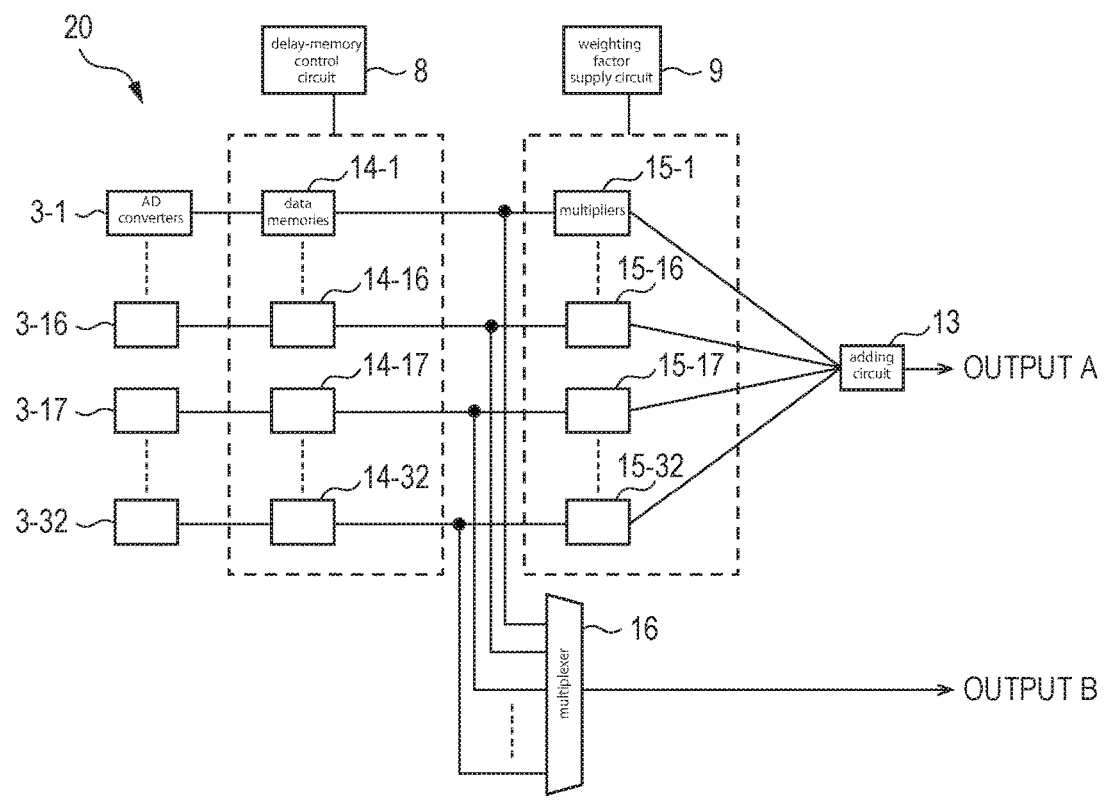
FIG. 4 is a diagram illustrating a configuration of a signal processing module according to the first embodiment of the present invention.

FIG. 4 is a diagram illustrating a configuration of a signal processing module 20. In FIG. 4, an example is illustrated in which the signal processing module 20 is constituted by 32 channels (chs).

The signal processing module 20 according to the first embodiment includes multiple analog-to-digital (AD) converters 3-1 to 3-32, a delay-memory control circuit 8, a weighting factor supply circuit 9, an adding circuit 13, data memories 14-1 to 14-32, multipliers 15-1 to 15-32 for apodization, and a multiplexer 16.

Each of the receiving devices in the device array 30 illustrated in FIG. 3 is connected to a corresponding one of the AD converters 3-1 to 3-32 illustrated in FIG. 4. For example, when the signal processing module 20 illustrated in FIG. 4 is the signal processing module 20-1 illustrated in FIG. 2, the receiving devices (1, 1) to (1, 32) illustrated in FIG. 3 are connected to the AD converters 3-1 to 3-32, respectively. Each of the received signals obtained through digital conversion performed by the AD converters 3-1 to 3-32 is stored in a corresponding one of the data memories 14-1 to 14-32.

Now, a method will be described in which image data is obtained by performing delay-and-sum processing on the basis of the received signals.

The delay-memory control circuit 8 computes data memory addresses which are necessary for the delay-and-sum processing on the basis of delay information supplied from the CPU for control 10, and supplies the computed data memory addresses to the data memories 14-1 to 14-32. Pieces of the received digital data which correspond to any pixel or voxel in the specimen E are read out from the data memories 14-1 to 14-32 in accordance with the data memory addresses supplied by the delay-memory control circuit 8. The received digital signals which have been read out are output to the respective multipliers 15-1 to 15-32. Thus, the received signals which are in phase are output to the multipliers 15-1 to 15-32.

The weighting factor supply circuit 9 supplies optimal window function weighting factors to the multipliers 15-1 to 15-32 on the basis of any pixel or voxel coordinates in the specimen E. Each of the received digital signals which is supplied to a corresponding one of the multipliers 15-1 to 15-32 is multiplied by a window function weighting factor computed by the weighting factor supply circuit 9 for a corresponding one of the channels, and is output to the adding circuit 13.

The adding circuit 13 adds together the in-phase received signals obtained through the above-described processes, thereby outputting an output A which corresponds to the 32 channels and which has been subjected to the delay-and-sum processing.

A CPU, a graphics processing unit (GPU), a digital signal processor (DSP), or other hardware (not illustrated) which is provided as a higher level component performs, for example, luminance value conversion on the signal obtained through the delay-and-sum processing, so that image data is generated on the basis of the signal obtained through the delay-and-sum processing.

In the signal processing module 20, the weighting factor supply circuit 9 may supply a value of zero to some of the multipliers 15-1 to 15-32 which correspond to channels for which the delay-and-sum processing is not to be performed. Thus, the delay-and-sum processing can be performed by using only the channels for which the delay-and-sum processing is to be performed. This means that, instead of portions corresponding to the signal processing modules, the region of the device array 30 may be divided into portions corresponding to the channels, each of which is smaller than a signal processing module. The region of the device array 30 can be divided in any manner.

In the case where the delay-and-sum processing is performed in the signal processing modules 20-1 to 20-Z, when it is necessary to add together all of the data outputs which are obtained through the delay-and-sum processing and which are output from the signal processing modules 20-1 to 20-Z, adding processing may be appropriately performed in accordance with the system configuration.

Now, a method will be described in which an image is obtained by applying any algorithm other than the delay-and-sum algorithm and performing image reconstruction on the basis of received signals.

The CPU for control 10 controls the multiplexer 16 to read out a received digital signal that corresponds any pixel or voxel among the received digital signals stored in each of the data memories 14-1 to 14-32.

A CPU, a GPU, a DSP, or other hardware (not illustrated) which is provided as a higher level component performs any image reconstruction on the basis of the received digital signals which have been read out, so as to generate an image data signal. Then, the CPU or the like which is provided as a higher level component performs, for example, luminance value conversion on this image data signal, thereby generating an image corresponding to the image data signal obtained through any image reconstruction.

This configuration enables not only the delay-and-sum processing on the obtained received signals but also image reconstruction in which any algorithm is applied. Thus, a photoacoustic image and an ultrasonic image can be arbitrarily obtained on the basis of received signals.

Typically, when an ultrasonic image is generated, delay-and-sum processing is performed; and when a photoacoustic image is generated, image reconstruction is performed by applying another algorithm other than a delay-and-sum algorithm. For example, image reconstruction methods for generating a photoacoustic image include a back projection method in time domain or Fourier domain which is typically used in tomography techniques.

Naturally, when an ultrasonic image or a photoacoustic image is obtained, either of delay-and-sum processing and image reconstruction in which any algorithm is applied may be applied.

In addition, a multiplier 15 may be provided between a data memory 14 and the multiplexer 16, and the weighting factor supply circuit 9 may supply a value of zero to multipliers 15 corresponding to channels which are not used for image reconstruction, whereby an image data signal can be generated by using only signals from arbitrary channels.

Figure 5:
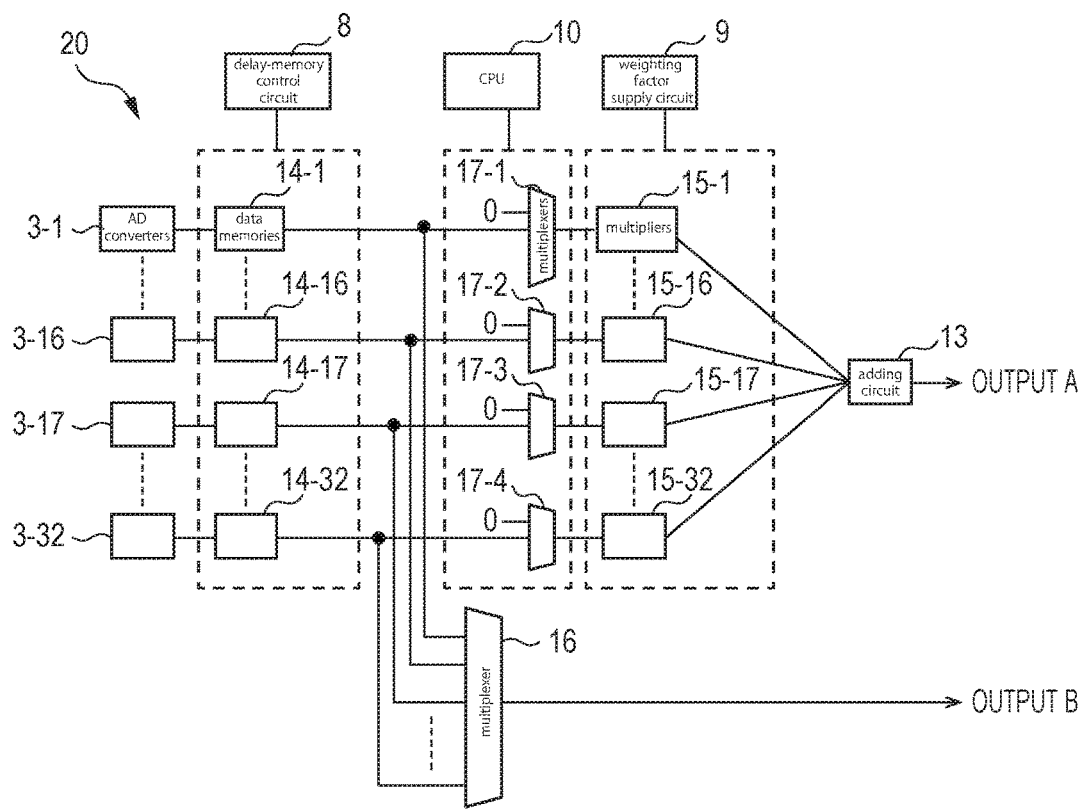
FIG. 5 is a diagram illustrating another exemplary configuration of the signal processing module according to the first embodiment of the present invention.

As illustrated in FIG. 5, multiplexers 17 are provided between data memories 14 and multipliers 15, whereby signals through arbitrary channels may be used for the delay-and-sum processing. In FIG. 5, multiplexers 17-1 to 17-32 each are switched on the basis of a channel division signal supplied by the CPU for control 10. This method enables the region of the device array 30 to be divided into portions corresponding to the channels. That is, channels in which multipliers 15 are to receive inputs can be selected by the multiplexers 17.

Alternatively, the multiplexers 17 may be disposed between the respective multipliers 15 and the adding circuit 13. In addition, the multiplexers 17 may be provided between the respective data memories 14 and the multiplexer 16, whereby image data may be generated through signal processing other than delay-and-sum processing by using signals from arbitrary channels.

In the present invention, the configuration of the signal processing module is not limited to the above-described configuration. A configuration may be employed in which multiple configurations described above are arranged in parallel in accordance with the allowable system scale so as to further enhance the capability of delay-and-sum processing.

According to the first embodiment, as described above, the signal processing on signals received in each of the regions A and B of the device array 30 illustrated in FIG. 3 is switched in accordance with the mode. The reason why signal processing is performed with the mode being switched as described above will be described below.

Figure 6:
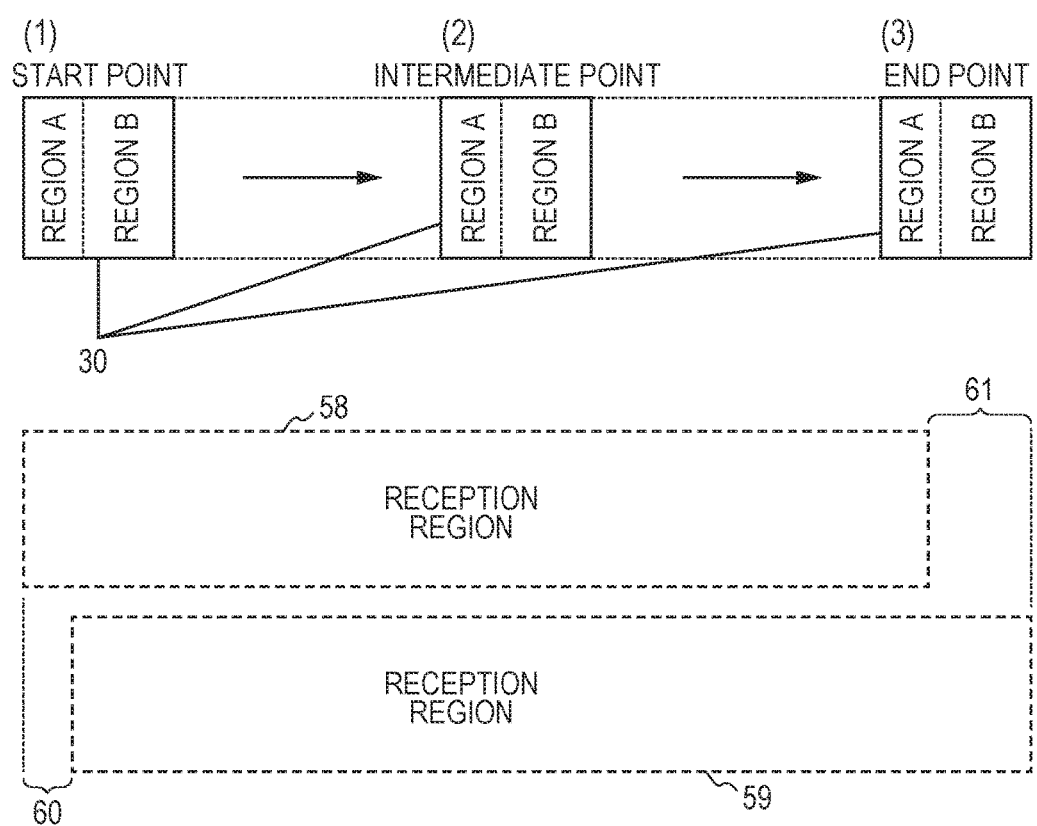
FIG. 6 is a diagram illustrating a receiving situation in the case where a mode is not switched.

FIG. 6 is a schematic diagram illustrating a receiving situation in which acoustic waves are received in the case where the mode is not switched. In this situation, the mechanical scanning mechanism 50 performs scanning with the device array 30 so as to move the device array 30. The signal processor 5 provides a setting in which a photoacoustic image is obtained on the basis of received signals which are output from the region A and in which an ultrasonic image is obtained on the basis of received signals which are output from the region B.

FIG. 6 illustrates a situation in which the regions A and B receive acoustic waves while the regions A and B are moving from a start point (1) through an intermediate point (2) to an end point (3) in a state where the regions A and B are located at certain relative positions. In this case, a reception region 58 corresponding to the region A is not the same as a reception region 59 corresponding to the region B. That is, in a region 60, received signals from the region A are obtained, but no received signals from the region B are obtained. In a region 61, received signals from the region B are obtained, but no received signals from the region A are obtained.

In this case, degradation occurs in image quality of an image which corresponds to a reception region in which received signals are not obtained as described above.

The specimen information acquisition apparatus is an apparatus which achieves one of its targets to obtain more accurate specimen information by integrating a photoacoustic image and an ultrasonic image. Accordingly, an image corresponding to a region, such as the region 60 or 61, in which received signals only from one of the regions A and B are obtained prevents the target of the apparatus to be achieved.

Accordingly, in the present invention, the mode is switched as described below so as to receive acoustic waves.

FIG. 7 is a diagram illustrating receiving situations which occur in the specimen information acquisition apparatus according to the first embodiment.

For example, in State 1, the signal processor 5 provides a setting in which a photoacoustic image is obtained on the basis of received signals which are output from the region A and in which an ultrasonic image is obtained on the basis of received signals which are output from the region B, on the basis of a control signal from the CPU for control 10 at the start point (1).

In State 2, the signal processor 5 provides a setting in which an ultrasonic image is obtained on the basis of received signals which are output from the region A and in which a photoacoustic image is obtained on the basis of received signals which are output from the region B, on the basis of the control signal from the CPU for control 10 at the start point (1).

In State 3, the signal processor 5 moves the device array 30 under a setting similar to that in State 2 and performs reception of acoustic waves. In State 3 in FIG. 7, a situation is illustrated in which the device array 30 passes through the intermediate point (2). In State 4, the signal processor 5 keeps a setting similar to that in State 2 until the device array 30 reaches the end point (3).

In State 5, the signal processor 5 provides a setting in which an ultrasonic image is obtained on the basis of received signals which are output from the region B, on the basis of the control signal from the CPU for control 10 at the end point (3).

The term "first mode" corresponds to the setting provided by the signal processor 5 in State 1; and the term "second mode" corresponds to the setting provided by the signal processor 5 in State 2.

The receiving devices arranged in the region A in State 1 correspond to a "first group"; and the receiving devices arranged in the region B correspond to a "second group". The receiving devices arranged in the region B in State 2 correspond to a "third group"; and the receiving devices arranged in the region A correspond to a "fourth group".

As illustrated in FIG. 7, the signal processor 5 can selectively operate in the first mode or the second mode, thereby reducing the difference between a reception region 36 which receives photoacoustic waves and a reception region 37 which receives the reflected waves of ultrasonic waves.

According to the first embodiment, as illustrated in State 5, there is a mode in which an ultrasonic image is obtained on the basis of received signals that are output from the region B and in which the region A is not used for image acquisition. In the present invention, the ability to selectively operate in the first mode or the second mode encompasses the ability for a signal processor to operate in another mode such as a mode which corresponds to the setting provided by the signal processor 5 in State 5.

The operations for the reception region for which the ultrasonic signal processing is performed and the reception region for which the photoacoustic signal processing is performed are not necessarily limited to the method illustrated in FIG. 7. As long as operations can be selectively made in the first mode or the second mode and a difference between the reception region 36 for an ultrasonic image and the reception region 37 for a photoacoustic image may be reduced, any operations are employable.

That is, the third group which corresponds to the photoacoustic signal processing in the second mode may include at least a group other than the first group which corresponds to the photoacoustic signal processing in the first mode. The fourth group which corresponds to the ultrasonic signal processing in the second mode may include at least a group other than the second group which corresponds to the ultrasonic signal processing in the first mode.

In the case where a range which is to receive acoustic waves is limited, scanning is not performed with the device array 30, and the device array 30 is fixed to receive acoustic waves.

According to the first embodiment, the mechanical scanning mechanism 50 is provided to move the probe 2, and scanning is mechanically performed on the skin surface of a living body. Alternatively, an inspector may hold the probe 2 so as to move the probe 2.

FIGS. 8A to 11B are diagrams illustrating the relationship in an operating sequence among the light irradiation, the processing for obtaining a photoacoustic image, i.e., the photoacoustic signal processing, and the processing for obtaining an ultrasonic image, i.e., the ultrasonic signal processing, in the specimen information acquisition apparatus 1 according to the first embodiment.

FIGS. 8A and 8B illustrate operating sequences in State 1 illustrated in FIG. 7. FIG. 8A illustrates an operating sequence in the region A, and FIG. 8B illustrates an operating sequence in the region B.

In FIG. 8A, upon the start of a measurement cycle, the light emitting unit 12 irradiates the specimen with light so that a photoacoustic image is obtained. Then, in photoacoustic signal processing A, the device array 30 receives photoacoustic waves produced by the specimen which has absorbed the light, and a photoacoustic image is generated on the basis of the received signals that are output from the region A of the device array 30.

In FIG. 8B, during the signal processing for generating a photoacoustic image in the photoacoustic signal processing A, the ultrasonic wave transmitter 11 transmits an ultrasonic wave to the specimen, and the reflected wave of the ultrasonic wave is received. An ultrasonic image is obtained on the basis of the received signals obtained by repeatedly performing the transmission/reception of an ultrasonic wave N times. That is, in State 1, the photoacoustic signal processing A and ultrasonic signal processing B are simultaneously performed.

Figure 9B:
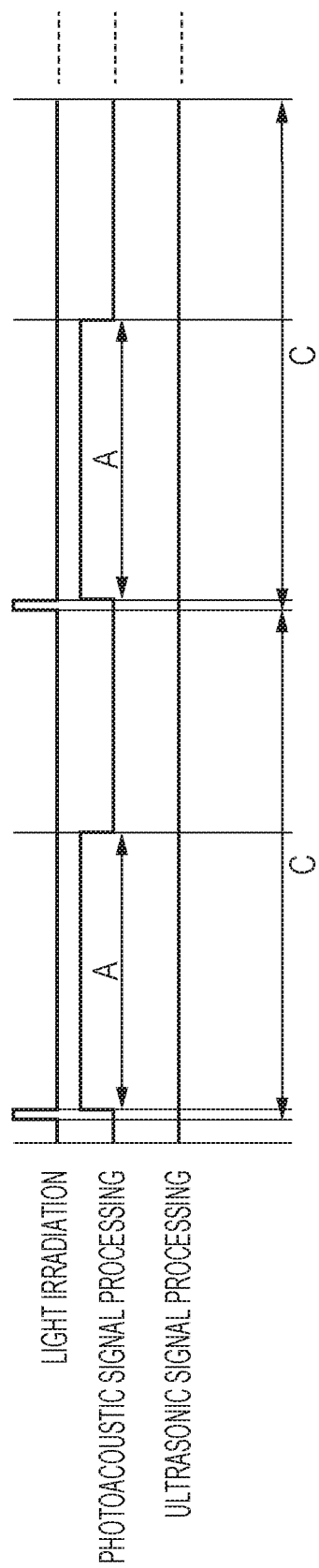
FIG. 9B is a diagram illustrating an operating sequence of the specimen information acquisition apparatus in States 2 to 4 illustrated in FIG. 7.

FIGS. 9A and 9B illustrate operating sequences in the regions A and B in States 2 to 4 illustrated in FIG. 7. In the region A illustrated in FIG. 9A, the ultrasonic signal processing B is performed. In the region B illustrated in FIG. 9B, the photoacoustic signal processing A is performed.

FIGS. 10A and 10B illustrate operating sequences in the regions A and B in State 5 illustrated in FIG. 7. In the region A illustrated in FIG. 10A, an image is not obtained from received signals. In the region B illustrated in FIG. 10B, the ultrasonic signal processing B is performed.

Thus, the photoacoustic signal processing and the ultrasonic signal processing are performed in parallel with each other, and the measurement cycles for the photoacoustic signal processing and the ultrasonic signal processing are sequentially performed, so that a photoacoustic image and an ultrasonic image are simultaneously obtained. In addition, the way of the division is changed as appropriate in which the region of the device array 30 is divided into the reception region that is used for the acquisition of a photoacoustic image and that for the acquisition of an ultrasonic image.

In the present invention, the chronological order in which the photoacoustic signal processing and the ultrasonic signal processing are performed is not necessarily the same as that illustrated in FIGS. 8A to 10B. As long as one of the signal processing operations does not adversely affect the other, any chronological order may be employed.

Figure 11B:
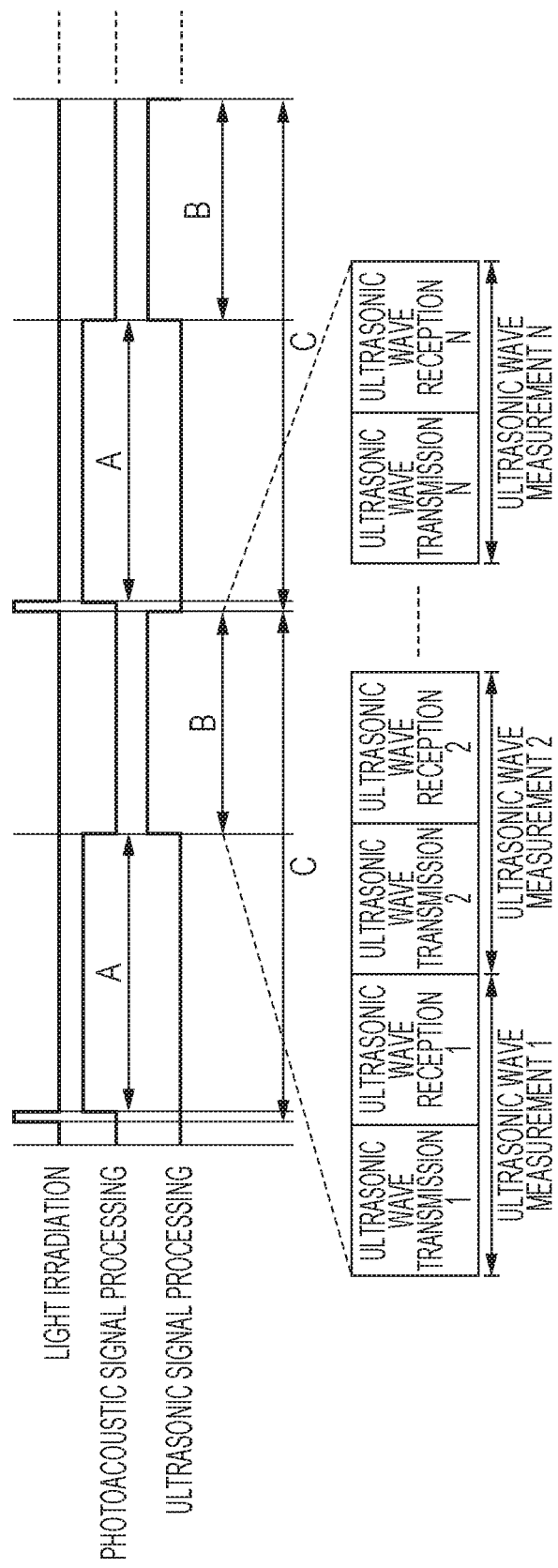
FIG. 11B is a diagram illustrating another exemplary operating sequence of the specimen information acquisition apparatus in States 2 to 4 illustrated in FIG. 7.

For example, FIGS. 11A and 11B illustrate an exemplary modification of operating sequences in States 2 to 4. In the region B illustrated in FIG. 11B, after the photoacoustic signal processing A ends, transmissions/receptions of an ultrasonic wave are performed, and an ultrasonic image corresponding to the region B is obtained through the ultrasonic signal processing B. In not only States 2 to 4 but also States 1 and 5, depending on the capability of the signal processing, upon satisfactory attenuation of photoacoustic waves that propagate in the specimen, the transmission/reception of an ultrasonic wave may be started, and the photoacoustic signal processing A and the ultrasonic signal processing B may be simultaneously performed.

In addition, in a particularly suspect region in diagnosis, mode in which all of the received signals from the device array are used to obtain a photoacoustic image or an ultrasonic image may be used. In this case, a photoacoustic image or an ultrasonic image having an improved contrast may be used in diagnosis in comparison with the case where a portion of the device array 30 is used to receive acoustic waves.

Furthermore, the way of the division of the device array 30 may be adjusted in accordance with the image quality that is required for a photoacoustic image or an ultrasonic image.

For example, more receiving devices may be allocated to an image which is to be obtained with a higher contrast, when signals are to be obtained.

When the photoacoustic signal processing is to be performed, it is necessary to set a reception region appropriately for photoacoustic waves in accordance with a degree in which light entering the specimen E is diffused in the specimen E. Accordingly, in accordance with the characteristics of the light emitting unit 12, the CPU for control 10 may control the process performed by the signal processor 5 so that the reception region for photoacoustic waves is appropriately set.

As described above, according to the first embodiment, the region of the device array of a probe is divided into regions for the photoacoustic signal processing and the ultrasonic signal processing, and the way of the division of the region can be flexibly changed. Accordingly, a difference between the reception region for photoacoustic waves and that for ultrasonic waves can be reduced. In addition, the signal processing method used in the apparatus is flexibly changed in accordance with the type of an image to be obtained, enabling various needs to be met.

Second Embodiment

Figure 12:
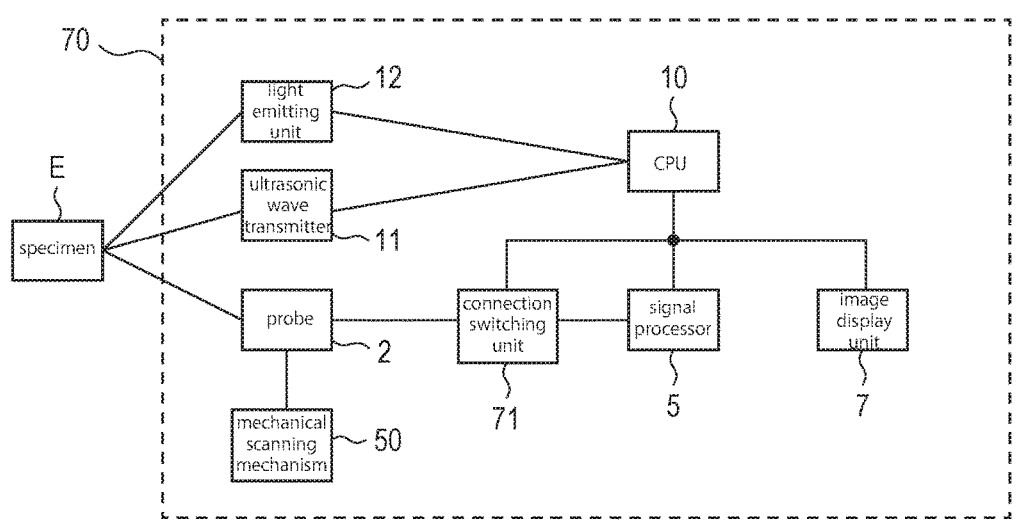
FIG. 12 is a diagram illustrating a configuration of a specimen information acquisition apparatus according to a second embodiment of the present invention.

FIG. 12 is a diagram illustrating a configuration of a specimen information acquisition apparatus according to a second embodiment of the present invention.

A specimen information acquisition apparatus 70 in FIG. 12 is different from that according to the first embodiment in that a connection switching unit 71 is inserted between the probe 2 and the signal processor 5. According to the second embodiment, the connection state of the connection switching unit 71 is switched in accordance with frequency specification of received acoustic waves. In FIG. 12, the same component as that in FIG. 1 is designated with the same reference numeral, and will not be described in detail.

Operations of the connection switching unit 71 will be specifically described below.

In the field of ultrasonic imaging apparatuses, to suppress side lobes when a received beam is formed by means of delay-and-sum processing, it is generally known that the pitch between receiving devices is to be equal to or less than a half of the wavelength of a received ultrasonic wave. In the case of an ultrasonic wave apparatus, the frequency of an ultrasonic signal which ranges from several MHz to ten-odd MHz is typically used.

On the other hand, in the case of a photoacoustic imaging apparatus, the frequency of a photoacoustic wave produced by irradiating a human body with light is approximately 1 MHz.

For example, according to the second embodiment, assume that the center frequency of a photoacoustic wave is 1 MHz and that the center frequency of an ultrasonic wave is 3 MHz. Accordingly, according to the second embodiment, a probe is used which has a center frequency bandwidth of 3 MHz so as to conform to the center frequency of an ultrasonic wave.

However, the device pitch in the probe which has a center frequency bandwidth of 3 MHz is smaller than that required for a photoacoustic wave.

Accordingly, according to the second embodiment, the connection switching unit 71 is used to widen the device pitch effectively by regarding multiple receiving devices that are adjacent to each other as a single device when an acoustic wave is received which has a frequency that is several times as low as the frequency of the other wave.

Figure 13A:
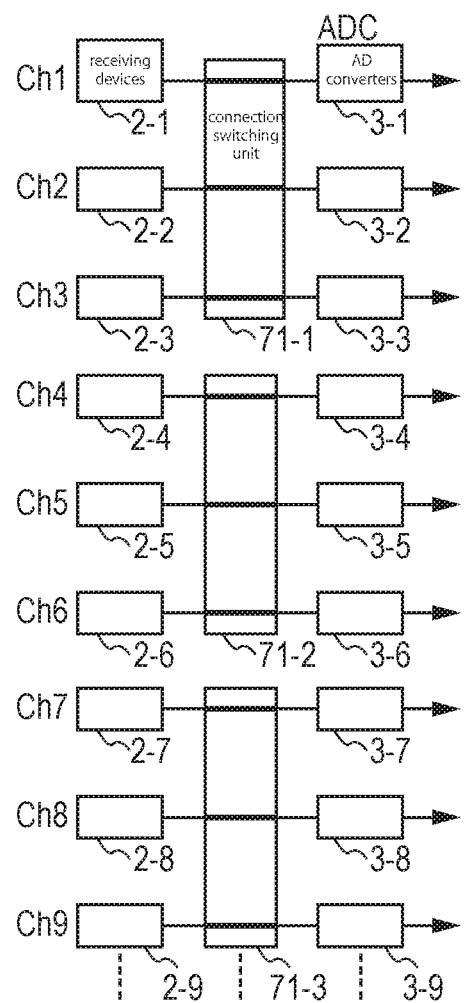
FIG. 13A is a diagram illustrating connection switching units and their connection states according to the second embodiment of the present invention.

FIGS. 13A and 13B are diagrams for explaining connection states of connection switching units according to the second embodiment. In FIGS. 13A and 13B, receiving devices 2-1 to 2-9 in the probe 2 are grouped in such a manner that three receiving devices are regarded as one set, and are connected to the AD converters 3-1 to 3-9 via connection switching units 71-1 to 71-3. The receiving devices 2-1 to 2-9 are provided with the device pitch which conforms to an ultrasonic signal having a center frequency of 3 MHz.

For example, when ultrasonic waves of 3 MHz are received, the receiving devices 2-1 to 2-9 arranged in the probe 2 are individually connected to the AD converters 3-1 to 3-9, respectively, as illustrated in FIG. 13A. The received signals of the ultrasonic waves which are received by the receiving devices 2-1 to 2-9 are converted into digital signals by the AD converters 3-1 to 3-9, and the resulting digital signals are stored in the data memories 14-1 to 14-N. The received digital signals of the ultrasonic waves which are stored in the data memories 14-1 to 14-N are output to the adding circuit 13 so as to be subjected to the delay-and-sum processing.

When photoacoustic waves of 1 MHz are received, the connection switching unit 71-1 connects the receiving devices 2-1 to 2-3 to each other as illustrated in FIG. 13B. The connection switching unit 71-1 is connected to each of the AD converters 3-1 to 3-3.

That is, the received signals which are output from the receiving devices 2-1 to 2-3 are added together by the connection switching unit 71-1. The signal obtained through the addition performed by the connection switching unit 71-1 is supplied to each of the AD converters 3-1 to 3-3. Thus, the signal to noise (SN) ratio of the signal is increased by means of the addition of the received signals performed by the connection switching unit 71-1.

In the addition performed by the connection switching unit 71-1, the added signals are out of phase. Therefore, this operation is different from the delay-and-sum processing. All of the signals supplied to the AD converters 3-1 to 3-3 are the same.

Similarly, the receiving devices 2-4 to 2-6, and 2-7 to 2-9, the connection switching units 71-2 and 71-3, and the AD converters 3-4 to 3-6, and 3-7 to 3-9 are connected to each other, respectively.

The configuration as illustrated in FIG. 13B enables the device pitch to be widened effectively by making one group from three receiving devices that are adjacent to each other and regarding the group as a single device. Each group of the AD converters 3-1 to 3-3, 3-4 to 3-6, and 3-7 to 3-9 outputs signals that are substantially the same, and the output signals are stored into the data memories 14-1 to 14-N.

The signals obtained by widening the device pitch effectively as described above are used for image reconstruction, so that a photoacoustic image is generated. Thus, a photoacoustic image suitable for photoacoustic waves of 1 MHz can be formed.

According to the second embodiment, a connection switching unit combines three receiving devices that are adjacent to each other and connects the combined receiving devices with three AD converters. However, the configuration is not limited to this. A configuration may be employed in which a connection switching unit is connected to one, two, or four or more AD converters.

The number of devices that are combined into one group is not necessarily three. As long as side lobes are suppressed, any number of devices may be combined into one group.

In addition, it is not necessary to combine devices only when photoacoustic waves are received. In accordance with a situation, devices may be combined when ultrasonic waves are received. Furthermore, the connection switching unit 71 may be included in the probe 2.

The connection switching unit 71 may add together the outputs from the AD converters 3 which are connected to the receiving devices that are regarded as a single device effectively, and the resulting output may be stored in the data memories 14. For example, the connection switching unit 71 is inserted between the AD converters 3-1 to 3-9 and the data memories 14-1 to 14-N, and adds together the outputs from the AD converters 3-1 to 3-3. The addition result is output to each of three data memories. Similarly, outputs from each group of the AD converters 3-4 to 3-6 and 3-7 to 3-9 are added together, and the addition result is output to each of three data memories that correspond to the group. This configuration causes the received signals received by three AD converters to be superimposed on top of one another, improving the SN ratio.

Similarly to the first embodiment, the region of the device array of a probe is divided into regions for the photoacoustic signal processing and the ultrasonic signal processing, and the way of the division of the region can be flexibly changed in the second embodiment. Thus, a difference between the reception region for photoacoustic waves and that for ultrasonic waves can be reduced. In addition, the signal processing method used in the apparatus may be flexibly changed in accordance with the type of an image to be obtained, enabling various needs to be met.

In addition, the adjacent receiving devices are combined and the received signals are added together, so that the occurrence of side lobes can be suppressed in a photoacoustic wave image and an ultrasonic wave image by using the same probe even when a photoacoustic wave and an ultrasonic wave have different center frequencies.

There are various methods for displaying an image according to the first and second embodiments of the present invention (not illustrated). For example, a photoacoustic image and an ultrasonic image which have been generated may be displayed so as to be superimposed one on top of the other, or one of the images may be separately displayed. Alternatively, the two images may be individually displayed in parallel on a monitor. In the case where subtle image information may be lost when photoacoustic image data and ultrasonic image data are synthesized so as to be superimposed one on top of the other and displayed, a photoacoustic image and an ultrasonic image are alternately displayed in the same region on a monitor, and correspondence between the images may be observed. In this case, a display ratio at which the images are alternately displayed and at which an inspector feels optimal for diagnosis depends on an inspection target or the contrast of the generated images. Accordingly, a test mode may be provided in which, upon inspection, the display ratio at which the images are alternately displayed is continuously varied, so that an inspector can select a display ratio at which the inspector feels optimal. It is desirable that the display ratio at which the images are alternately displayed be recorded in the apparatus along with the image data so that the display can be reproduced.

As described above, desirable embodiments are described. However, the present invention is not limited to these embodiments. Various modifications or applications are encompassed as long as they do not depart from the scope of the claims.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-138797, filed Jun. 22, 2011, which is hereby incorporated by reference herein in its entirety.

REFERENCE SIGNS LIST

1 specimen information acquisition apparatus
2 probe
5 signal processor
7 image display unit
11 ultrasonic wave transmitter
12 light emitting unit
50 mechanical scanning mechanism
E specimen

The invention claimed is:

1. An object information acquisition apparatus comprising:
    a plurality of receiving elements that outputs received signals in response to a reception of a photoacoustic wave propagated from an object irradiated with light or in response to a reception of a reflected wave reflected by the object;
    a moving unit that moves the plurality of receiving elements; and
    a signal processor that obtains a photoacoustic image on the basis of the received signals due to the photoacoustic wave or an ultrasonic image on the basis of the received signals due to the reflected wave, and that selectively performs an operation in a first mode and an operation in a second mode on the received signals obtained at each of a plurality of positions to which the plurality of receiving elements is moved,
    the operation in the first mode being an operation in which, the photoacoustic image is obtained on the basis of received signals output from a first group of receiving elements among the plurality of receiving elements, and the ultrasonic image is obtained on the basis of received signals output from a second group of receiving elements among the plurality of receiving elements and different from the first group of receiving elements, and
    the operation in the second mode being an operation in which, the photoacoustic image is obtained on the basis of received signals that are output from a third group of receiving elements among the plurality of receiving elements and different from the first group of receiving elements, and the ultrasonic image is obtained on the basis of received signals that are output from a fourth group of receiving elements among the plurality of receiving elements and different from the second group of receiving elements.

2. The object information acquisition apparatus according to claim 1,
    wherein the moving unit moves the plurality of receiving elements in a first direction from a first position to a second position,
    further wherein the signal processor performs the operation in the first mode at the first position and performs the operation in the second mode at the second position.

3. The object information acquisition apparatus according to claim 2, wherein the plurality of receiving elements are arranged along the first direction.

4. The object information acquisition apparatus according to claim 1, wherein the signal processor performs delay-and-sum processing on the received signals that are output from the second group of receiving elements or the received signals that are output from the fourth group of receiving elements.

5. The object information acquisition apparatus according to claim 1, wherein the signal processor performs image reconstruction to generate the photoacoustic image on the basis of the received signals that are output from the first group of receiving elements or the received signals that are output from the third group of receiving elements.

6. The object information acquisition apparatus according to claim 5, wherein the image reconstruction is a back projection method.

7. The object information acquisition apparatus according to claim 1, wherein the signal processor adds together the received signals that are output from the plurality of receiving elements.

8. The object information acquisition apparatus according to claim 7, wherein the signal processor adds together received signals that are output from mutually adjacent receiving elements in the first group of receiving elements or mutually adjacent receiving elements in the third group of receiving elements.

9. The object information acquisition apparatus according to claim 1, wherein the signal processor converts the received signals that are output from the plurality of the receiving elements into digital signals.

10. The object information acquisition apparatus according to claim 1, wherein the plurality of receiving elements are capacitive micromachined ultrasonic transducers.

11. The object information acquisition apparatus according to claim 1, wherein the receiving elements of the third group are identical to those of the second group and the receiving elements of the fourth group are identical to those of the first group.

12. The object information acquisition apparatus according to claim 1, wherein the second group of receiving elements or the fourth group of receiving elements is structured to receive the reflected wave while the signal processor is performing a signal processing for obtaining the photoacoustic image on the basis of the received signals that are output from the first group of receiving elements or the third group of receiving elements.

13. The object information acquisition apparatus according to claim 1, wherein the plurality of receiving elements forms a two-dimensional array.

14. The object information acquisition apparatus according to claim 1, further comprising:
a transmitting element configured to transmit the ultrasonic wave; and
a light emitting unit configured to emit the light.

15. The object information acquisition apparatus according to claim 14, wherein at least one of the plurality of the receiving elements serves as the transmitting element.

16. The object information acquisition apparatus according to claim 1, further comprising:
an image display unit configured to display the photoacoustic image or the ultrasonic image.

17. An object information acquisition method comprising:
receiving received signals from a plurality of receiving elements;
forming a first photoacoustic image on the basis of received signals due to a reception of a photoacoustic wave from an object output from a first group of receiving elements among a plurality of receiving elements;
forming a first ultrasonic image on the basis of received signals due to a reflected wave from the object output from a second group of receiving elements among the plurality of receiving elements and different from the first group of receiving elements;
forming a second photoacoustic image on the basis of received signals output from a third group of receiving elements among the plurality of receiving elements and different from the first group of receiving elements; and
forming a second ultrasonic image on the basis of received signals output from a fourth group of receiving elements among the plurality of receiving elements and different from the second group,
wherein forming the first photoacoustic image, the first ultrasound image, the second photoacoustic image, and the second ultrasound image are performed for each of a plurality of positions the plurality of receiving elements are moved to with respect to the object.

18. The object information acquisition method according to claim 17, further comprising:
adding together the received signals that are output from mutually adjacent receiving elements in the first group of receiving elements or mutually adjacent receiving elements in the second group of receiving elements.

19. An object information acquisition apparatus comprising:
a signal processor that obtains a photoacoustic image on the basis of received signals due to a photoacoustic wave or an ultrasonic image on the basis of received signals due to a reflected wave, the received signals being signals output from a plurality of receiving elements in response to a reception of a photoacoustic wave propagated from an object irradiated with light or in response to a reception of a reflected wave reflected by the object, the plurality of receiving elements being moved to a plurality of positions;
wherein the signal processor selectively performs, for each of a plurality of positions at which the plurality of receiving elements is moved, an operation in a first mode and an operation in a second mode on the received signals, wherein
the operation in the first mode being an operation in which, the photoacoustic image is obtained on the basis of received signals output from a first group of receiving elements among the plurality of receiving elements, and the ultrasonic image is obtained on the basis of received signals output from a second group of receiving elements among the plurality of receiving elements and different from the first group of receiving elements, and
the operation in the second mode being an operation in which, the photoacoustic image is obtained on the basis of received signals that are output from a third group of receiving elements among the plurality of receiving elements and different from the first group of receiving elements, and the ultrasonic image is obtained on the basis of received signals that are output from a fourth group of receiving elements among the plurality of receiving elements and different from the second group of receiving elements.

20. The object information acquisition apparatus according to claim 19, wherein the signal processor performs delay-and-sum processing on the received signals that are output from the second group of receiving elements or the received signals that are output from the fourth group of receiving elements.

21. The object information acquisition apparatus according to claim 19, wherein the signal processor performs image reconstruction to generate the photoacoustic image on the basis of the received signals that are output from the first group of receiving elements or the received signals that are output from the third group of receiving elements.

22. The object information acquisition apparatus according to claim 21, wherein the image reconstruction is a back projection method.

23. The object information acquisition apparatus according to claim 19, wherein the signal processor adds together the received signals that are output from the plurality of receiving elements.

24. The object information acquisition apparatus according to claim 23, wherein the signal processor adds together received signals that are output from mutually adjacent receiving elements in the first group of receiving elements or mutually adjacent receiving elements in the third group of receiving elements.

25. The object information acquisition apparatus according to claim 19, wherein the signal processor converts the received signals that are output from the plurality of the receiving elements into digital signals.

26. The object information acquisition apparatus according to claim 19, wherein the receiving elements of the third group are identical to those of the second group and the receiving elements of the fourth group are identical to those of the first group.

* * * * *